(12) United States Patent
Surma

(10) Patent No.: US 6,322,564 B1
(45) Date of Patent: Nov. 27, 2001

(54) PROXIMAL ALIGNMENT INSERTION GUIDE AND METHOD THEREFOR

(75) Inventor: Gabriel Surma, Winona Lake, IN (US)

(73) Assignee: DePuy Orthopaedics, Inc., Warsaw, IN (US)

(*) Notice: Subject to any disclaimer, the term of this patent is extended or adjusted under 35 U.S.C. 154(b) by 0 days.

(21) Appl. No.: 09/332,733

(22) Filed: Jun. 14, 1999

Related U.S. Application Data

(60) Provisional application No. 60/089,721, filed on Jun. 18, 1998.

(51) Int. Cl.[7] .................................. A61F 2/46; A61F 2/38
(52) U.S. Cl. .................................................. 606/79; 606/89
(58) Field of Search .................................. 606/79, 80, 81, 606/82, 85, 86–89; 623/20

(56) References Cited

U.S. PATENT DOCUMENTS

| | | | |
|---|---|---|---|
| 1,985,108 | * 12/1934 | Rush | ..................... 128/346 |
| 3,793,650 | 2/1974 | Ling et al. . | |
| 4,012,796 | 3/1977 | Weisman et al. . | |
| 4,285,071 | 8/1981 | Nelson et al. . | |
| 4,404,692 | 9/1983 | Eftekhar . | |
| 4,417,571 | 11/1983 | Nelson et al. . | |
| 4,523,587 | 6/1985 | Frey . | |
| 4,566,138 | 1/1986 | Lewis et al. . | |
| 4,770,660 | 9/1988 | Averill . | |
| 4,783,192 | 11/1988 | Wroblewski et al. . | |
| 4,827,919 | 5/1989 | Barbarito et al. . | |
| 4,881,536 | 11/1989 | Nobel et al. . | |
| 5,116,380 | 5/1992 | Hewka et al. . | |
| 5,480,453 | 1/1996 | Burke . | |
| 5,624,445 | * 4/1997 | Burke | ..................... 606/89 |
| 5,658,291 | * 8/1997 | Techiera | ..................... 606/80 |
| 5,888,245 | * 3/1999 | Meulink et al. | ..................... 623/23 |
| 6,080,155 | * 6/2000 | Michelson | ..................... 606/61 |

OTHER PUBLICATIONS

DePuy, Inc., John Callaghan, M.D., Dennis Lennox, M.D., David Fisher, M.D., Douglas Kilgus, M.D., Endurance™ Surgical Technique, ©1994.

* cited by examiner

Primary Examiner—Paul J. Hirsch
(74) Attorney, Agent, or Firm—Maginot, Addison & Moore

(57) ABSTRACT

A kit for centering proximally an implant within a canal formed in a femur is provided. The kit includes a cutter apparatus adapted to form a reference in a resected surface of the femur and a guide adapted to support the implant and formed for extension into the reference to align the implant within the canal. The cutter apparatus includes a body formed to include first and second ends and teeth extending from the second end. The teeth are positioned in a predetermined pattern to form the reference when the cutter apparatus is moved relative to the femur. In addition, the guide includes a handle, a clamp coupled to the handle and formed with jaws adapted to engage the implant, and an extension extending from at least one of the jaws. The extension is received within the reference to align the implant within the canal.

19 Claims, 5 Drawing Sheets

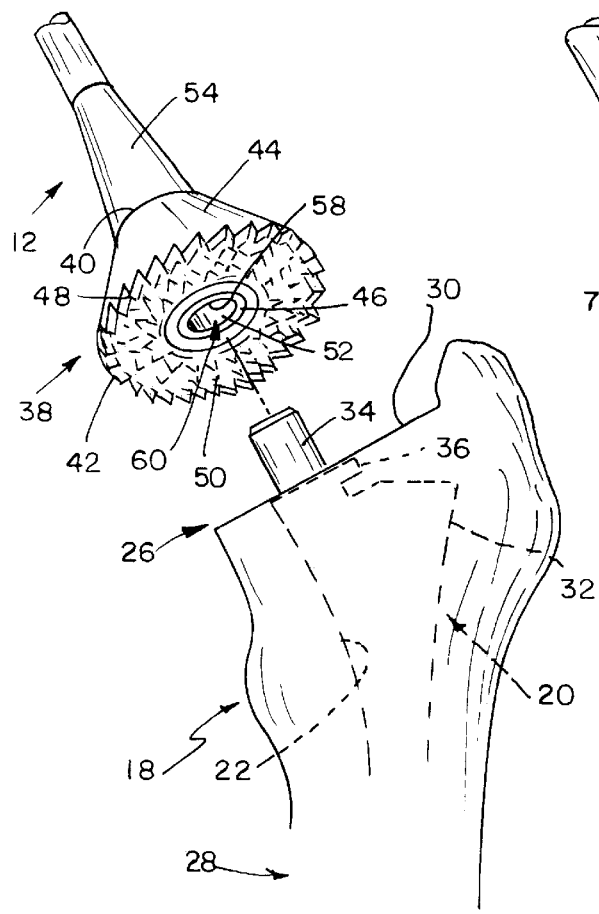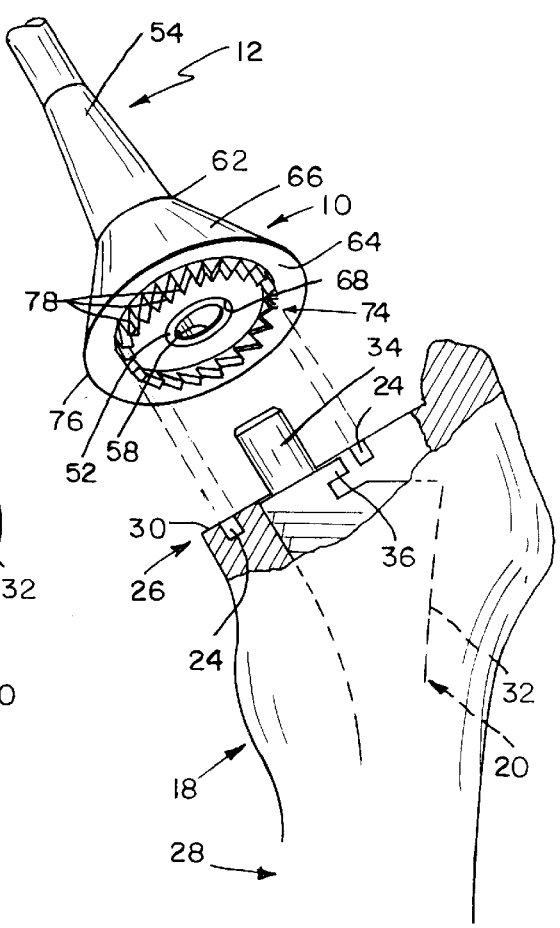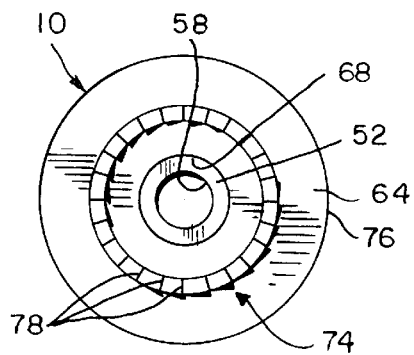

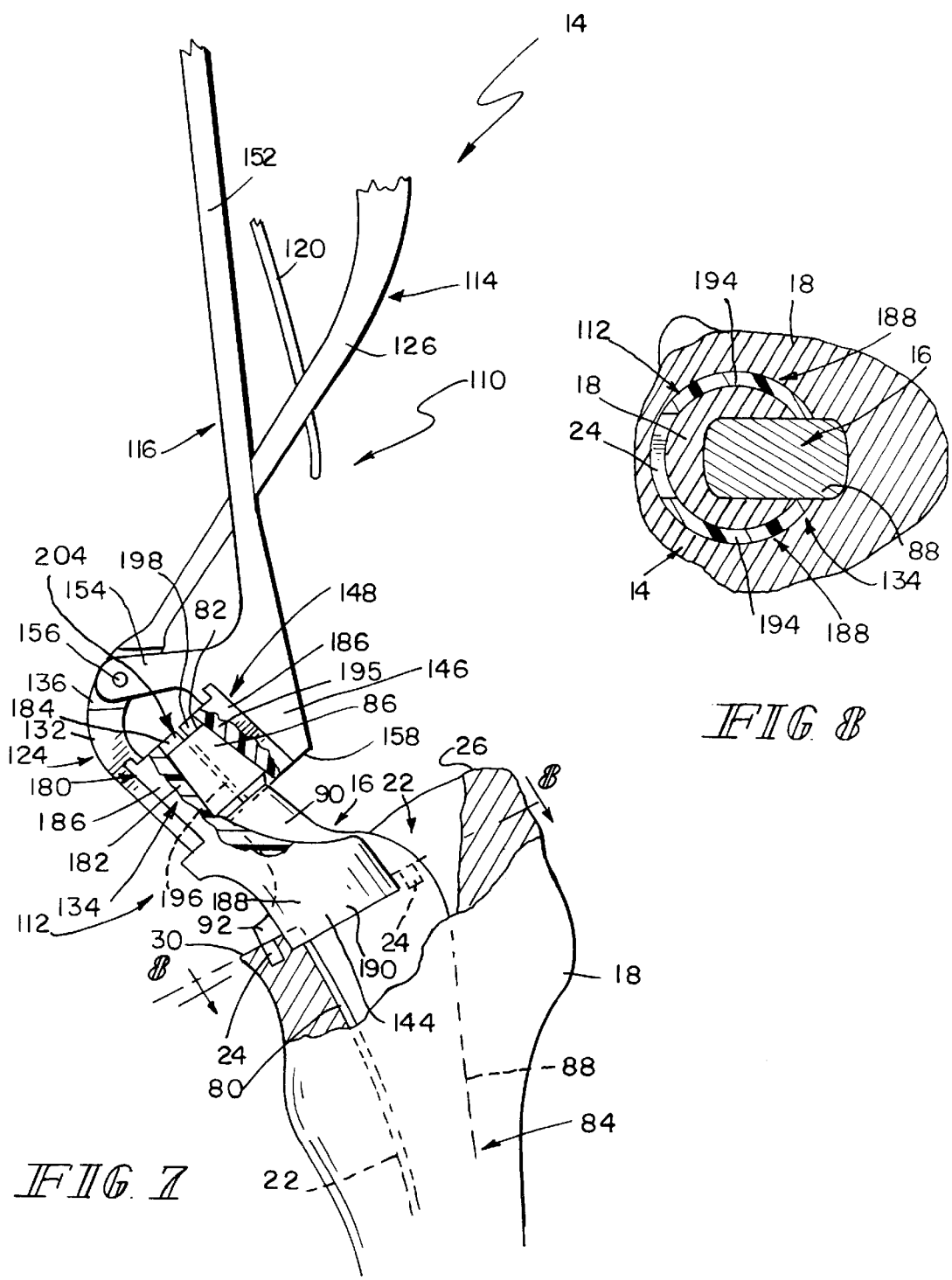

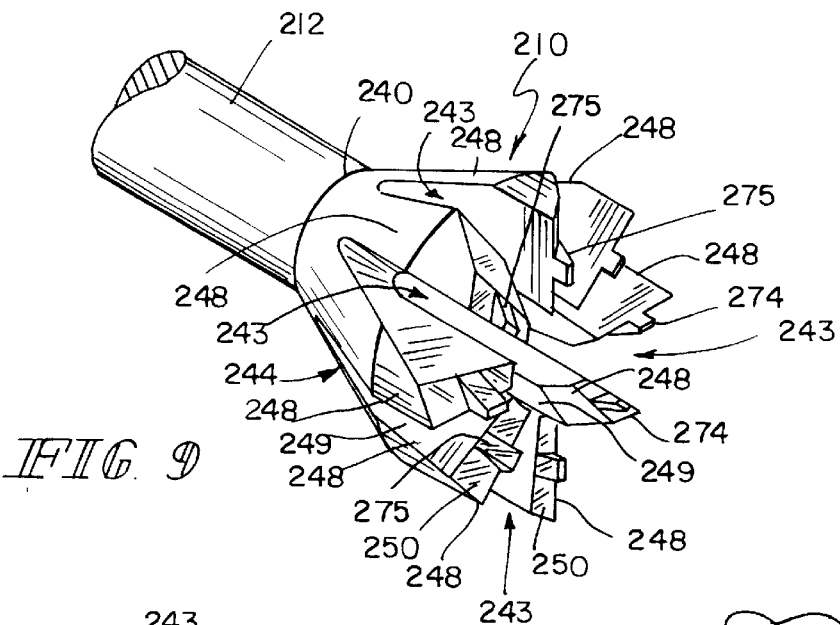
FIG. 9
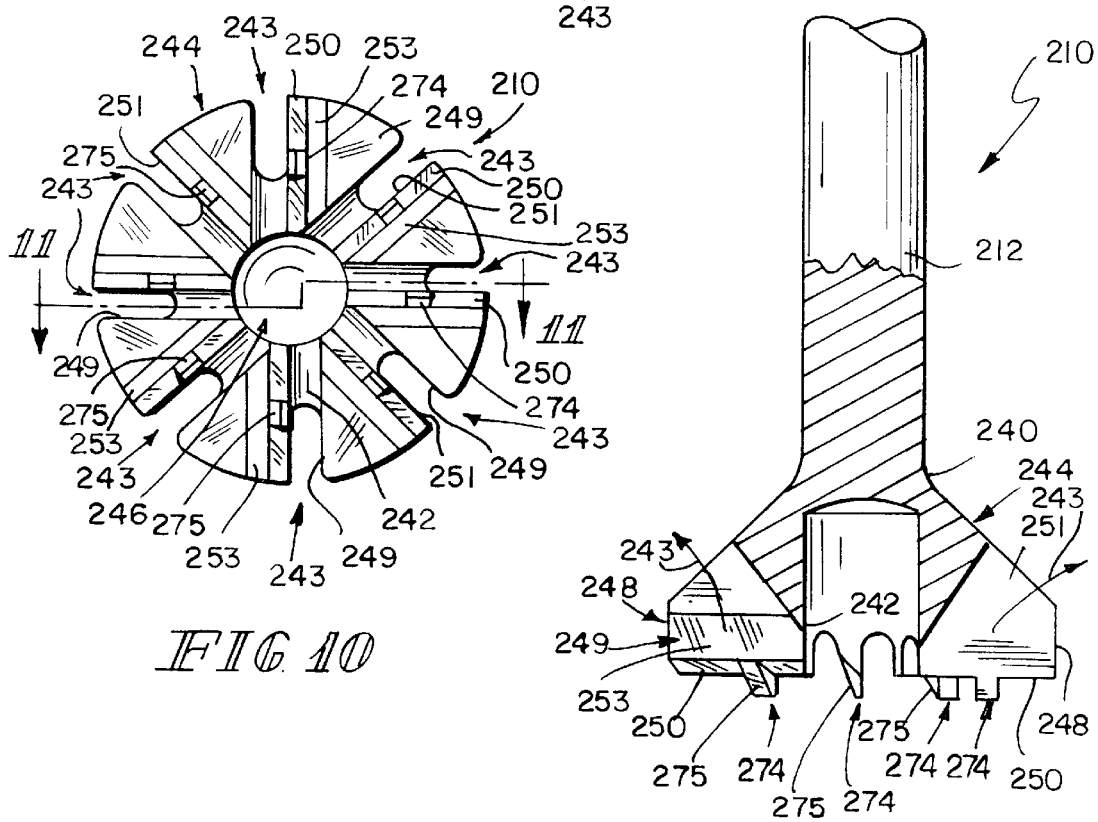
FIG. 10
FIG. 11

PROXIMAL ALIGNMENT INSERTION GUIDE AND METHOD THEREFOR

This application claims priority under 35 U.S.C. §119(e) of Serial No. 60/089,721 filed Jun. 18, 1998 in the United States Patent and Trademark Office.

BACKGROUND AND SUMMARY OF THE INVENTION

The present invention relates to an insertion guide apparatus and method of use of the guide apparatus, and particularly to an apparatus configured to align proximally a femoral prosthesis in an intramedullary canal and method of using said apparatus. More particularly, the present invention relates to an apparatus and method for forming a reference that positions a prosthesis in the intramedullary canal and using the reference to align proximally the prosthesis within the canal of the femur.

Prosthesis are often used to replace the femoral head and acetabulum of the hip in such instances of fracture or chronic arthritis. See for example the pamphlet entitled "Surgical Technique Total Hip System Endurance™" by DePuy Inc., 1994 and U.S. Pat. No. 5,286,260 entitled "Modular Hip Prosthesis", to Richard Bolesky. In a conventional hip replacement surgery, a femoral head is removed from a femur, a hollow cavity is drilled into the femur, and a conventional implant is cemented within the cavity. A conventional acetabular cup is also cemented in place within the acetabulum of the hip.

According to the present invention, a calcar cutter apparatus is provided for forming a reference in a resected surface of a femur. The apparatus comprises a body formed to include a first end and a second end and teeth extending from the first end. The teeth are positioned to be in a pre-determined pattern to form a reference in a femur. Preferably, the teeth are positioned to lie in a row in the shape of ring. In addition, the teeth may be positioned to lie in a spaced-apart relationship relative to one another and channels may be positioned to lie between the teeth. A secondary tooth may also extend from each tooth.

According to another embodiment of the invention, an apparatus is provided for aligning a femoral implant within a femur having a canal and a reference formed in the femur spaced apart from the canal. The apparatus includes a handle and a clamp coupled to the handle. The clamp includes jaws adapted to engage the implant and an extension extending from at least one of the jaws. The extension is adapted to be received within the reference to align the implant within the canal. Preferably, the extension includes outer and inner surfaces and a rim that extends between the surfaces and is adapted to be received in the reference of the femur.

In addition, a kit is provided for centering proximally an implant within a canal formed in a femur. The kit includes a calcar cutter adapted to form a reference in a resected surface of the femur and a guide adapted to support the implant. The guide is also formed for extension into the reference to align the implant within the canal. Preferably, the calcar cutter includes a body having teeth extending from the body. The teeth lie in a pre-determined series relative to one another spaced-apart from the perimeter of the body. The guide includes a handle and a clamp coupled to the handle. The handle has jaws adapted to engage selectively the implant and an extension extending from one of the jaws. The extension is adapted to be received within the reference to align the implant within the canal.

A method for aligning proximally an implant within a canal of a femur is also provided in accordance with the present invention. The method includes the steps of forming a reference in a resected surface of the femur, providing an alignment insertion guide for holding an implant, positioning at least a portion of the guide in the reference so that the implant extends into the canal of the femur in a pre-determined aligned position.

Additional features and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

FIG. 1 is a perspective view showing a conventional calcar mill attached to a calcar handle and a resected femur having a broach implanted therein that aligns the calcar mill upon the femur and limits a depth that the calcar mill can plane the femur;

FIG. 2 is a perspective view with portions broken away after the femur has been planed by the calcar mill showing a calcar cutter in accordance with the present invention attached to the calcar handle, the calcar cutter including teeth that form a reference in the planed surface of the femur;

FIG. 3 is a bottom view of the calcar cutter of FIG. 2 coupled to the calcar handle showing the calcar cutter having an end and teeth extending from the end;

FIG. 7 is a side elevation view with portions broken away of the femur and the insertion instrument of FIG. 6 after the insertion instrument has gripped the implant and the broach has been removed from the femur, showing the insertion instrument centering the implant within a femoral canal by aligning the jaws with the reference previously formed in the planed surface of the femur;

FIG. 8 is a view taken along lines 8—8 of FIG. 7 showing the implant situated in the canal and the jaws of the implant situated within the reference;

FIG. 9 is a perspective view of an alternative embodiment of a cutter apparatus in accordance with the present invention, showing the cutter apparatus including a body having planing teeth extending a first pre-determined distance therefrom and a guide tooth extending from each planing tooth;

FIG. 10 is an end view of the calcar cutter of FIG. 9 showing eight spaced-apart planing teeth and channels positioned to lie between the planing teeth; and FIG. 11 is a view taken along lines 11—11 of FIG. 10 showing a clean-out path of bone through the channels.

DETAILED DESCRIPTION OF THE DRAWINGS

Figure 4:
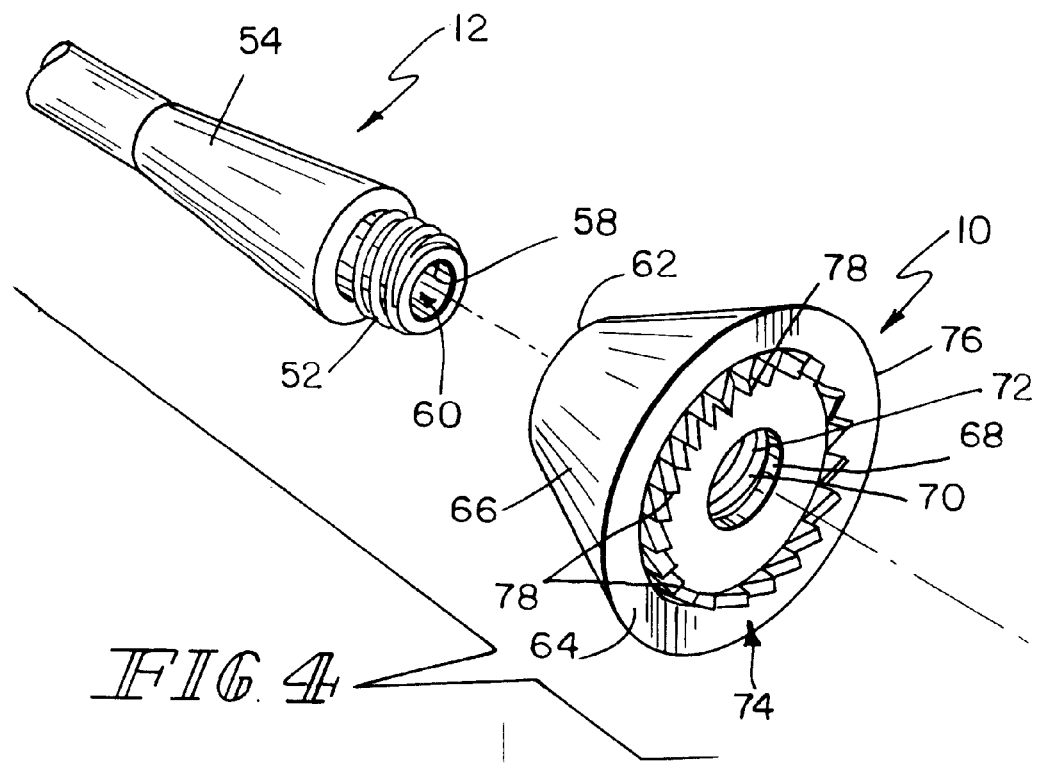
FIG. 4 is an exploded perspective view of the calcar cutter and handle of FIGS. 2 and 3 showing the handle having a threaded end and the cutter having a threaded interior that corresponds with the threaded end to couple the handle and cutter together.

In accordance with the present invention a proximal alignment insertion kit and method are provided that utilize a cutter apparatus or calcar cutter 10 and an alignment insertion guide 14 to align proximally a conventional prosthetic femoral implant 16 within a femur 18 during hip replacement surgery. Steps involved in hip replacement surgery are known to one in the ordinary skill in the art and set out, for example, in the pamphlet entitled "Surgical Technique Total Hip System Endurance™" by DePuy Inc., the text of which is incorporated herein by reference. Cutter 10 and guide 14 of the present invention are used by the surgeon following resection of a femoral head (not shown) and insertion of a broach 20 into a femoral canal 22. Particularly, calcar cutter 10 of the present invention forms a reference 24 in femur 18 while insertion guide 14 utilizes reference 24 to align implant 16 within canal 22. While reference 24 is illustratively a groove, it is understood that reference 24 may be any number of guides, recesses, slots, or holes formed in femur 18 in accordance with the present invention.

Resected femur 18 is shown in FIG. 1 as it would appear to a surgeon as femur 18 is being prepared to receive implant 16 within canal 22. Femur 18 includes a proximal end 26, a distal end 28, a resected surface 30 adjacent to proximal end 26, and canal 22 drilled through resected surface 30 and into femur 18. Broach 20 is positioned to lie within femoral canal 22 after resection of surface 30. Broach 20 includes a body 32, a head 34, and a limit rib 36 positioned to lie between body and head 32, 34. Broach 20 provides the surgeon with an alignment tool for planing femur 18 as well as a depth limit tool for ensuring that femur 18 is planed to a predetermined depth. While broach 20 is illustrated and described, it is understood that any number of broaches having a variety of shapes and sizes may be used in accordance with the present invention.

Implant 16 is coupled to femur 18 once broach 20 has been removed from canal 22. Implant 16 includes a proximal end 82 and a distal end 84. Implant 16 is also formed to include a head 86 adjacent to proximal end 82, a body 88, and a stem 90 extending between and coupling with head 86 and body 88. Body 88 also includes a lip 92. While implant 16 is illustrated and described, it is within the scope of the present disclosure to form implant 16 in a variety of shapes and sizes.

A conventional calcar mill 38 that is attached to a conventional calcar handle 12 is also provided to plane resected surface 30. See FIG. 1. Calcar mill 38 includes first and second surfaces 40, 42 and a truncated cone or body 44 extending between surfaces 40, 42. Calcar mill 38 also includes an aperture 46 that extends between first surface 40 and second surface 42. As shown in FIG. 1, teeth 48 extend from second surface 42. Teeth 48 are formed to include a pointed tip 50 for disrupting surface 30 and planing femur 18 to a generally level surface in alignment with limit rib 36 of broach 20. In addition, aperture 46 of calcar mill 38 is defined by a threaded inner wall (not shown) that provides a threaded connection between mill 38 and handle 12. Milling is accomplished by rotating handle 12 and mill 38 clockwise and can be done by hand or by connecting a stem 54 of handle 12 to a powered source (not shown). It is within the scope of this disclosure to form mill 38 for counterclockwise or translational movement relative to surface 30. While mill 38 is illustrated and described, it is within he scope of this disclosure to use any number of conventional calcar mills to plane femur 18.

As shown in FIG. 4, calcar handle 12 includes a threaded end 52 and stem 54 extends from threaded end 52. Threaded end 52 includes an inner surface 58 defining a hollow inner portion 60. Referring now to FIG. 1, threaded end 52 is sized for extension through aperture 46 of mill 38 to engage the threaded inner wall (not shown) of mill 38. Thus mill 38 is selectively coupled to handle 12. Inner surface 58 of threaded end 52 is sized for extension about head 34 of broach 20.

Figure 5:
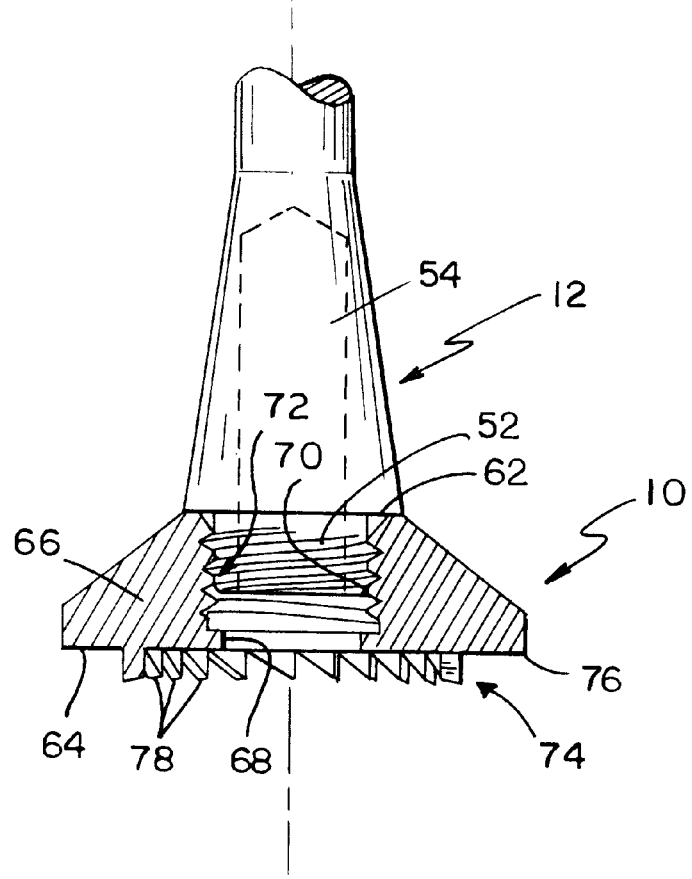
FIG. 5 is a sectional view of the calcar cutter and handle of FIGS. 2 and 3 showing the threaded coupling of the handle to the cutter and the teeth extending from the end of the cutter.

Calcar cutter 10 in accordance with the present invention is selectively coupled to handle 12 once conventional mill 38 has been removed. See FIGS. 2–5. Cutter 10 is configured to form reference 24 within milled surface 30 to provide a location marker for guide 14. Cutter 10 includes a first end 62 spaced apart from a second end 64, a truncated cone or body 66 extending between ends 62, 64, and an aperture 68 formed to extend through body 66 from first end 62 to second end 64, as shown in FIGS. 2, 3, 4 and 5. Aperture 68 is defined by an inner surface 70 having inner threads 72 formed thereon. As shown in FIGS. 4 and 5, threads 72 are formed for alignment with threaded end 52 of handle 12. Thus, aperture 68 of cutter 10 receives threaded end 52 of handle 12 to couple cutter 10 to handle 12. It is within he scope of this disclosure to couple cutter 10 and handle 12 together using snaps, friction fit, adhesives or the like.

Cutter 10 is also formed to include a ring of teeth 74 extending from second end 64. Teeth 74 are positioned to lie spaced-apart from aperture 68 and an outer perimeter 76 of second end 64. As shown in FIGS. 2, 4 and 5, teeth 74 include pointed tips 78 that are formed to disrupt surface 30 in order to form reference 24. It is within the scope of this disclosure to vary the number and location of teeth 74 on second end 64. In addition, while teeth 74 are illustrated and described, it is within he scope of this disclosure to have any number of cutting apparatuses extending from second end 64 to cut surface 30. Cutter 10 is constructed of stainless steel, although it is within he scope of this disclosure to construct cutter 10 from a wide variety of materials such as titanium or other metal alloys.

Figure 6:
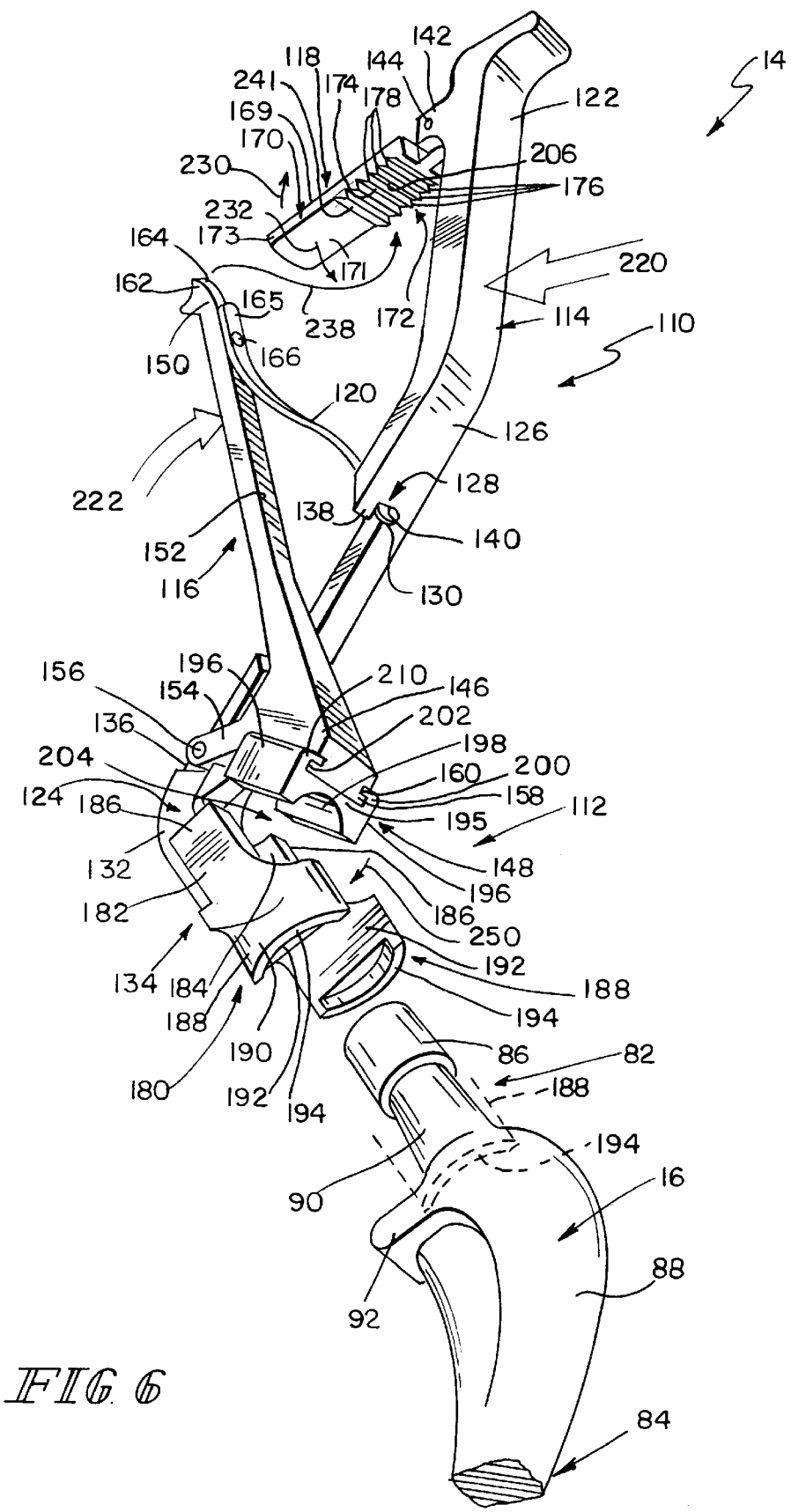
FIG. 6 is a perspective view of an insertion instrument in accordance with the present invention and a prosthetic implant showing the insertion instrument including a clamp and a set of jaws that cooperate with the clamp to grasp a head of the implant.

Teeth 74 of cutter 10 form reference 24 which is sized to receive guide 14 therein. Guide 14 includes a handle 110 and an opposite clamp 112. Guide 14 is formed so that clamp 112 couples with implant 16, as shown in FIG. 7, and aligns with reference 24 to insert and center implant 16 within femoral canal 22. As shown in FIG. 6, handle 110 includes a first plier arm 114, a second plier arm 116, a lock mechanism 118 pivotably coupled to first plier arm 114, and a spring 120 extending between first and second plier arms 114, 116. First plier arm 114 has an outer end 122, an inner end 124, and a center portion 126 extending between outer and inner ends 122, 124. Center portion 126 of first plier arm 114 includes a spring grip 128 that receives a first end 130 of spring 120. Spring grip 128 includes a tab 138 that extends from center portion 126 and defines a notch 140. Inner end 124 of first pilar arm 114 includes a pivot portion 132 for coupling with clamp 112, as will be described later in more detail. Inner end 124 of first plier arm 114 is also formed to include an arm-pivot portion 136, as shown in FIG. 7, that is configured to receive second plier arm 116. Arm-pivot portion 136 is positioned to lie between pivot portion 132 and center portion 126. Outer end 122 of first plier arm 114 also includes spaced-apart tabs 142 and a pivot pin 144 extending therethrough. Tabs 142 and pivot pin 144 are formed to receive lock mechanism 118, as will be described later in more detail.

Second plier arm 116 is pivotably coupled to first pilar arm 114 and includes an inward end 146, an outward end 150, and a center portion 152 extending therebetween. Inward end 146 includes arms 154 extending therefrom for engagement with arm-pivot portion 136 of first plier arm 114. A pivot pin 156 extends through arms 154 and pivot portion 136 so that first plier arm 114 is pivotally coupled to second plier arm 116. Inward end 146 of second plier arm 116 additionally includes a tab 158 forming a groove 160. Tab 158 and groove 160 are coupled with clamp 112, as shown in FIGS. 6 and 7.

Outward end 150 of second plier arm 116 includes a tip 162 having a curved cam surface 164 for camming engagement with lock mechanism 118. A second end 165 of spring 120 is coupled by a screw 166 to outward end 150 of second plier arm 116. Spring 120 acts normally to bias outward and outer ends 150, 122 of first and second plier arms 114, 116 away from one another and guide 14 toward an opened and unlocked position, as shown in FIG. 6. While spring 120 is illustrated and described, it is within the scope of this disclosure to use a variety of springs or living hinges to yieldably bias outward end 150 of second plier arm 116 away from outer end 122 of first plier arm 114. Additionally, a headed rivet, rot, pin, or comparable connection device may be used to couple second end 165 of spring 120 to outward end 150 of second plier arm 116 rather than screw 166, as shown in FIG. 6.

Lock mechanism 118 is provided and is coupled, as mentioned above, to outer end 122 of first plier arm 114 by pivot pin 144. Lock mechanism 118 includes a smooth tab portion 170 and a ratchet portion 172. See FIG. 6. Tab portion 170 includes an outer surface 169 facing away from clamp 112, an opposite inner lock surface 171, and opposite edges 173 extending between surfaces 169,171. Ratchet portion 172 is coupled to plier arm 114 by pivot pin 144 so that tab portion 170 may move relative to first plier arm 114. A spring (not shown) is formed to extend between lock mechanism 118 and first plier arm 114 normally to bias inner locking surface 171 toward clamp 112. Ratchet portion 172 is also formed to include multiple teeth 174 each forming peaks 176 and valleys 178 positioned to lie between peaks 176. Valleys 178 receive and retain tip 162 of outward end 150 of second plier arm 116 to maintain guide 14 in a locked position (FIG. 7) as will be described later in the operation of lock mechanism 118.

Clamp 112 of guide 14 includes a jaw 180 that has first and second jaw members 134, 148 that cooperate to receive head 86 of implant 16 therebetween. First jaw member 134 includes a body 182 having opposite side walls 186 and a curved inner surface 184 therebetween. Jaw member 134 additionally includes an extension member 188 extending from each side wall 186. Extension members 188 are spaced-apart from one another and are formed to include an outer surface 190, a curved inner surface 192, and a semicircular rim 194 extending between surfaces 190, 192. Rims 194 are formed to be received within reference 24 formed by calcar cutter 10 in resected and milled surface 30 of femur 18, as shown in FIGS. 7 and 8.

Second jaw member 148 of clamp 112 additionally includes a body 195 having opposite side walls 196 and a curved inner surface 198 extending therebetween. As shown in FIG. 6, curved inner surfaces 184, 198 are generally concave in shape and define a generally partially cylindrical cavity 240 therebetween when guide 14 is in a locked position. See FIGS. 7 and 8. Each side wall 196 includes a lip 210 forming a channel 212 therein. Tab 158 of inward end 146 of second plier arm 116 is formed to be received within channel 212 while each lip 210 of second jaw member 148 is formed to be received within groove 160, as shown in FIG. 6. Thus, second jaw member 148 is coupled to second plier arm 116.

The method in accordance with the present invention includes the step of coupling cutter 10 to handle 12 once conventional mill 38 has been removed from handle 12. Cutter 10 is then placed upon planed resected surface 30 of femur 18 such that head 34 of broach 20 extends through aperture 68 of cutter 10. At this time, teeth 74 are in contact with resected and milled surface 30. By rotating handle 12 and cutter 10 either by power source or by hand, teeth 74 are moved to cut guide reference 24 in surface 30 of femur 18 as shown, for example, in FIG. 2. While cutter 10 is shown to cut reference 24 in the shape of an annular groove, it is within the scope of this disclosure that guides, recesses, slots, holes, or grooves may be cut or otherwise formed in femur 18 to serve as reference 24.

Once reference 24 is present in surface 30, broach 20 is removed from femur 18 and steps may be taken in the surgical procedure to irrigate canal 22 left by broach 20 and inject cement 80 into canal 22 in accordance with well-known surgical techniques. As mentioned above, guide 14 aligns or centers implant 16 within femoral canal 22. Head 86 and stem 90 of implant 16 are placed within clamp 112 of guide 14 so that inner surfaces 192 of extension members 188 surround and engage body 88 and stem 90 of implant 16 as shown in FIG. 7 and in phantom in FIG. 6. Head 86 is positioned to lie within cylindrical cavity 240 created between inner surfaces 184, 198 of first and second jaw members 134, 148, respectively. Handle 110 Of guide 14 is then squeezed so that first and second plier arms 114, 116 are moved in directions 220, 222, respectively until guide 14 is positioned to lie in locked position where tip 162 of second plier arm 116 is situated within any valley 178 of teeth 174 of lock mechanism 118. See FIG. 7.

As plier arms 114, 116 are urged closed in directions 220, 222, respectively, plier arms 114, 116 are also urged to pivot about pivot pin 156 to urge first and second jaw members 134, 148 of clamp 112 toward the locked position of guide 14 as indicated by arrow 250 and shown in FIG. 6. As first and second plier arms 114, 116 are being moved toward each other, tip 162 engages tab portion 170 of lock mechanism 118. As both plier arms 114, 116 continue to move in directions 220, 222, respectively, cam surface 164 of tip 162 allows tip 162 to ramp up tab portion 170 and slide along surface 171. Lock mechanism 118, as mentioned before, is pivotable about pivot pin 144. Lock mechanism 118 is pivotable in both a rearward direction 230 and a forward direction 232. As cam surface 164 is urged to ramp up tab portion 170, lock mechanism 118 is urged to pivot slightly in rearward direction 230. Upon further movement of handle 110 toward the locked position of guide 14, cam surface 164 is urged to ramp up cam surfaces 242 of teeth 174 until tip 162 is positioned to rest in any valley 178 of the surgeon's discretion. This motion is illustrated by arrow 238 in FIG. 6. Once tip 162 is positioned to rest in any one of valleys 178 of teeth 174, guide 14 is positioned to lie in the locked position. Upon the surgeon's release of plier arms 114, 116 once guide 14 is in the locked position, guide 14 will remain in the locked position. At this time, both inner surfaces 184, 198 are positioned to engage head 86 of implant 16.

Once first and second jaw members 134, 148 have been closed around head 86 and tip 162 is positioned to lie within any one of valleys 178 formed by teeth 174 of lock mechanism 118, implant 16 is ready to be inserted within canal 22 of resected femur 18. See FIG. 7. To align implant 16 within femoral canal 22, rims 194 of extension members 188 are placed within reference 24 formed by calcar cutter 10 in surface 30 of femur 18, as shown in FIG. 8.

By aligning rims 194 of guide 14 in reference 24 of resected surface 30 of femur 18, the surgeon can be assured that implant 16 is properly centered within femoral canal 22.

The alignment of guide 14 in reference 24 insures a uniform thickness of the cement mantle between implant 16 and femur 18. In order to release tip 162, lock mechanism 118 is rotated in rearward direction 230 and spring 120 then acts to bias guide 14 toward the unlocked position. See FIG. 6.

As shown in FIG. 9, an alternative cutter apparatus 210 is provided in accordance with the present invention for planing femur 18 and forming reference 24. Cutter apparatus 210 includes a handle 212 and a body 244 having a first end 240 coupled to handle 254 and a second end 242. Referring now to FIGS. 10 and 11, body 244 also includes an aperture 246 that extends into second end 242. As shown in FIGS. 9 and 10, eight planing teeth 248 extend from second end 242 in a star-burst pattern. Planing teeth 248 are spaced-apart from one another and a channel 243 extends therebetween. Channels 243 are offset from planing teeth 248 to allow bone chips, shavings, etc. (not shown) to be removed from apparatus 210. While planing teeth 248 are illustrated and described, it is within the scope of this disclosure to have teeth with any number of patterns, such as the pattern illustrated in FIG. 1.

Referring now to FIG. 9, each planing tooth 248 includes a first cutting wall 249 and an opposite second cutting wall 251. Cutting wall 249 includes a tapered surface 253 and a cutting tip 250 extending between surface 253 and second wall 251. Each first cutting wall 249 is configured to shave surface 30 and plane femur 18 to a generally level surface in alignment with limit rib 36 of broach 20 during clockwise rotation of body 244. Rotation of body 244 can be done by hand or by connecting handle 212 to a powered source (not shown). It is within the scope of this disclosure to provide tips 250 of apparatus 210 that are formed for counter-clockwise or translational movement relative to surface 30. It is also within the scope of this disclosure to vary the number and location of planing teeth 248.

As shown in FIG. 9, each planing tooth 248 of apparatus 210 further includes a guide tooth 274 thereon. Each guide tooth 274 includes a cutting surface 275 that is formed to disrupt surface 30 in order to form reference 24. The number and location of teeth 274 on planing teeth 248 may vary. In addition, while teeth 274 are illustrated and described, it is within the scope of this disclosure to have any number of cutting apparatuses extend from planing teeth 248. Apparatus 210 is constructed of stainless steel, although it is within the scope of this disclosure to construct apparatus 210 from a wide variety of materials such as titanium or other metal alloys.

Cutter apparatus 210 in accordance with the present invention is thus capable of planing femur 18 and forming reference 24 in one step. For example, apparatus 210 is placed upon planed resected surface 30 such that head 34 of broach 20 extends through aperture 246 of body 244. At this time, planing teeth 248 and guide teeth 274 engage resected surface 30. By rotating handle 212 either by power source or by hand, planing teeth 248 are moved to shave bone and form a planed surface 30 on femur 18. Simultaneously, guide teeth 274 are moved to cut reference 24 in surface 30 of femur 18. During rotation, shaved bone is removed from apparatus 210 through channels 243 as is shown by arrows 290. While cutter apparatus 210 is shown to cut reference 24 in the shape of an annular groove, it is within the scope of this disclosure that guides, recesses, slots, holes, or grooves may be cut or otherwise formed in femur 18 to serve as reference 24.

Although the invention has been described in detail with reference to certain preferred embodiments, variations and modifications exist within the scope and spirit of the invention as described and defined in the following claims.

What is claimed is:

1. A kit for centering proximally an implant within a canal formed in a femur, the kit comprising:
    a cutter apparatus adapted to form a reference in a resected surface of the femur, and
    a guide adapted to support the implant and formed for extension into the reference to align the implant within the canal,
    wherein the cutter apparatus includes a body and teeth extending from the body, and
    wherein the teeth are positioned to lie in a ring-shaped series relative to one another.

2. The kit of claim 1, wherein the body includes an outer perimeter and the teeth are spaced-apart from the perimeter.

3. The kit of claim 1, wherein the cutter apparatus includes a first end, a second end, and the teeth extend from the second end.

4. The kit of claim 3, wherein the cutter apparatus is formed to include a threaded aperture extending between the first end and the second end and wherein the threaded aperture is adapted to receive a handle therein.

5. The kit of claim 3, wherein the second end includes an outer perimeter and the teeth are positioned to lie spaced-apart from the outer perimeter.

6. The kit of claim 1, wherein the guide includes a handle and a clamp coupled to the handle and adapted to engage selectively the implant.

7. The kit of claim 6, wherein the clamp includes opposing jaw members selectively defining a cavity therebetween which is configured to receive a head of the implant therein.

8. A kit for centering proximally an implant within a canal formed in a femur, the kit comprising:
    a cutter apparatus adapted to form a reference in a resected surface of the femur, and
    a guide adapted to support the implant and formed for extension into the reference to align the implant within the canal,
    wherein the guide includes a handle having a first arm, a second arm, a lock mechanism coupled to the first arm, and a spring formed to extend between the first and second arms to bias normally the handle in an opened position in which the first arm is spaced-apart from the lock mechanism.

9. The kit of claim 8, wherein the guide includes a first jaw member coupled to the first arm and a second jaw member coupled to the second arm and the first and second jaw members selectively define a cavity therebetween sized to receive the implant therein.

10. A kit used during an implant procedure, comprising:
    a cutter having a plurality of teeth which are positioned relative to one another in a ring-shaped arrangement, said plurality of teeth being configured to cut a ring-shaped reference in a resected surface of a bone, and
    a holding and guiding tool configured to (i) hold an implant, and (ii) extend into the ring-shaped reference cut by the cutter to align the implant within a canal of the bone.

11. A kit used during an implant procedure, comprising:
    a cutter configured to cut a ring-shaped reference in a resected surface of a bone, and
    a holding and guiding tool having a first jaw member and a second jaw member which are movable in relation to each other, wherein (i) said first jaw member and said second jaw member are configured to cooperate with each other to hold said implant therebetween, and (ii) at least one of said first jaw member and said second jaw member includes a curved extension configured to be received in said ring-shaped reference.

12. The kit of claim 11, wherein said at least one of said first jaw member and said second jaw member includes a sidewall and a curved rim which extends from said sidewall.

13. The kit of claim 11, wherein:

said cutter includes a plurality of teeth which are positioned to lie in a ring-shaped series relative to one another, and said curved extension is substantially semi-circular shaped.

14. A kit used during an implant procedure, comprising:

a cutter configured to cut a ring-shaped reference in a resected surface of a bone, and a guide tool having a first plier arm and a second plier arm which pivot in relation to each other, wherein (i) said first plier arm includes a first jaw member, and said second plier arm includes a second jaw member, (ii) said first jaw member and said second jaw member are configured to cooperate with each other to hold said implant therebetween, (iii) said first jaw member includes a first extension configured to be received in a first portion of said ring-shaped reference, and (iv) said first jaw member further includes a second extension configured to be received in a second portion of said ring-shaped reference.

15. The kit of claim 14, wherein:

said first jaw member includes a first sidewall, said first extension includes a first curved rim which extends from said first sidewall, said first jaw member further includes a second sidewall, and said second extension includes a second curved rim which extends from said second sidewall.

16. The kit of claim 15, wherein said first curved rim is spaced apart from said second curved rim.

17. The kit of claim 14, wherein:

said cutter includes a plurality of teeth which are positioned to lie in a ring-shaped series relative to one another, said first extension is substantially semi-circular shaped, and said second extension is substantially semi-circular shaped.

18. A kit used during an implant procedure, comprising:

a cutter configured to cut a reference in a resected surface of a bone, and a guide tool having a first plier arm and a second plier arm which pivot in relation to each other, wherein (i) said first plier arm includes a first jaw member, and said second plier arm includes a second jaw member, (ii) said first jaw member and said second jaw member cooperate with each other to hold said implant therebetween, and (iii) at least one of said first jaw member and said second jaw member includes a sidewall and an extension which extends from said sidewall and is configured to be received in said reference.

19. The kit of claim 18, wherein:

said cutter includes a plurality of teeth which are positioned to lie in a ring-shaped series relative to one another, and said extension is substantially semi-circular shaped.

* * * * *